US00PP24857P3

(12) United States Plant Patent
Beekenkamp

(10) Patent No.: US PP24,857 P3
(45) Date of Patent: Sep. 9, 2014

(54) ***CELOSIA* PLANT NAMED 'BKCELOR'**

(50) Latin Name: *Celosia hybrida*
Varietal Denomination: BKCELOR

(71) Applicant: Annie Cornelia Beekenkamp, Maasdijk (NL)

(72) Inventor: Annie Cornelia Beekenkamp, Maasdijk (NL)

(73) Assignee: Beekenkamp Plants, B.V., Maasdijk (NL)

( * ) Notice: Subject to any disclaimer, the term of this patent is extended or adjusted under 35 U.S.C. 154(b) by 87 days.

(21) Appl. No.: 13/694,149

(22) Filed: Oct. 31, 2012

(65) Prior Publication Data

US 2014/0123356 P1 May 1, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — C. A. Whealy

(57) ABSTRACT

A new and distinct cultivar of *Celosia* plant named 'BKCELOR', characterized by its upright plant habit; freely basal branching habit; medium green elliptic leaves; freely flowering habit; dark orange-colored flowers arranged on conical compound spikes; and good interior and garden performance.

2 Drawing Sheets

Botanical designation: *Celosia hybrida.*
Cultivar denomination: 'BKCELOR'.

BACKGROUND OF THE INVENTION

The present invention relates to a new and distinct *Celosia* plant, botanically known as *Celosia hybrida* and hereinafter referred to by the name 'BKCELOR'.

The new *Celosia* plant is a product of a planned breeding program conducted by the Inventor in Maasdijk, The Netherlands. The objective of the breeding program is to create new *Celosia* plants that have unique and attractive flowers, long flowering period and good interior and garden performance.

The new *Celosia* plant originated from an open-pollination in August, 2006 in Maasdijk, The Netherlands of a proprietary selection of *Celosia hybrida* identified as code number 1400247, not patented, as the female, or seed, parent with an unknown selection of *Celosia hybrida* as the male, or pollen, parent. The new *Celosia* plant was discovered and selected by the Inventor as a single flowering plant from within the progeny of the stated open-pollination in a controlled environment in Maasdijk, The Netherlands in August, 2007

Asexual reproduction of the new *Celosia* plant by cuttings in a controlled environment in Maasdijk, The Netherlands since January, 2009 has shown that the unique features of this new *Celosia* plant are stable and reproduced true to type in successive generations.

SUMMARY OF THE INVENTION

Plants of the new *Celosia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'BKCELOR'. These characteristics in combination distinguish 'BKCELOR' as a new and distinct *Celosia* plant:

1. Upright plant habit.
2. Freely basal branching habit.
3. Medium green elliptic leaves.
4. Freely flowering habit.
5. Dark orange-colored flowers arranged on conical compound spikes.
6. Good interior and garden performance.

Plants of the new *Celosia* differ from plants of the female parent selection in the following characteristics:

1. Plants of the new *Celosia* are taller than plants of the female parent selection.
2. Leaves of plants of the new *Celosia* are broader and lighter green in color than leaves of plants of the female parent selection.
3. Plants of the new *Celosia* and the female parent selection differ in flower color as plants of the female parent selection have light orange-colored flowers.

Plants of the new *Celosia* can be compared to plants of *Celosia hybrida* 'Flame', not patented. In side-by-side comparisons, plants of the new *Celosia* differed primarily from 'Flame' in the following characteristics:

1. Leaves of plants of the new *Celosia* were lighter green in color than leaves of plants of 'Flame'.
2. Plants of the new *Celosia* flowered earlier than plants of 'Flame'.
3. Plants of the new *Celosia* and 'Flame' differed in flower color as plants of 'Flame' had darker orange-colored flowers.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type. Colors in the photographs may differ slightly from the color values cited in the detailed botanical description which accurately describe the colors of the new *Celosia* plant.

The photograph on the first sheet comprises a side perspective view of a typical flowering plant of 'BKCELOR' grown in a container.

The photograph on the second sheet is a close-up view of a typical inflorescence of 'BKCELOR'.

DETAILED BOTANICAL DESCRIPTION

The aforementioned photographs and following observations, measurements and values describe plants grown in 12-cm containers during the winter and spring in a glass-covered greenhouse in Maasdijk, The Netherlands and under commercial cultural practices typical of *Celosia* production. During the production of the plants, day and night temperatures ranged from 19° C. to 20° C. Plants were pinched one time and were 13 weeks old when the photographs and description were taken. In the following description, color references are made to The Royal Horticultural Society Colour Chart, 2007 Edition, except where general terms of ordinary dictionary significance are used.

Botanical classification: *Celosia hybrida* 'BKCELOR'.

Parentage:

*Female, or seed, parent.*—Proprietary selection of *Celosia hybrida* identified as code number 1400247, not patented.

*Male, or pollen, parent.*—Unknown selection of *Celosia hybrida*, not patented.

Propagation:

*Type.*—By cuttings.

*Time to initiate roots, summer.*—About 16 days at temperatures ranging from 19° C. to 21° C.

*Time to initiate roots, winter.*—About 19 days at temperatures ranging from 19° C. to 21° C.

*Time to produce a rooted young plant, summer.*—About 21 days at temperatures ranging from 19° C. to 21° C.

*Time to produce a rooted young plant, winter.*—About 23 days at temperatures ranging from 19° C. to 21° C.

*Root description.*—Medium in thickness, fibrous; white in color.

*Rooting habit.*—Moderately freely branching; medium density.

Plant description:

*Plant form and growth habit.*—Herbaceous annual typically grown as a potted plant; upright plant habit; broad inverted triangle; freely branching habit with about seven basal branches developing per plant; moderately vigorous growth habit.

*Plant height.*—About 27 cm.

*Plant width (spread).*—About 26.5 cm.

*Branches.*—Length: About 16.9 cm. Diameter: About 6 mm. Internode length: About 1 cm. Texture: Smooth, glabrous. Color, developing: Close to 173D. Color, fully developed: Close to N172B to N172C.

Foliage description:

*Arrangement.*—Alternate; simple.

*Length.*—About 9.2 cm.

*Width.*—About 4.8 cm.

*Shape.*—Ovate.

*Apex.*—Acute to apiculate.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to 144A to 144B. Developing leaves, lower surface: Close to 146D. Fully expanded leaves, upper surface: Close to 137A to 137C; venation, close to 144B. Fully expanded leaves, lower surface: Close to 138B; venation, close to 146C to 146D.

*Petioles.*—Length: About 1.4 cm. Diameter: About 3 mm. Texture, upper and lower surfaces: Smooth, glabrous. Color, upper and lower surfaces: Close to 145C; towards the base, close to 18C.

Flower description:

*Flower type and arrangement.*—Single rotate flowers arranged in conical terminal and axillary compound spikes; flowers sessile; flowers face upright and outwardly.

*Flowering habit.*—Freely flowering habit with about 300 flowers per primary (terminal) inflorescence and about 30 flowers per secondary (axillary) inflorescence.

*Fragrance.*—Faint, slightly moldy.

*Natural flowering season.*—Plants begin flowering about 90 days after planting; flowering continuous from early April until the autumn in The Netherlands.

*Postproduction longevity.*—Inflorescences of the new *Celosia* have good longevity typically lasting about ten days on the plant; flowers not persistent.

*Inflorescence height.*—About 7 cm.

*Inflorescence diameter.*—About 4.8 cm.

*Flower diameter.*—About 3 mm.

*Flower height.*—About 5 mm.

*Flower buds.*—Length: About 4 mm. Diameter: About 1 mm. Shape: Ovoid. Color: Close to 25A to 25B; towards the base, close to 19D.

*Petals.*—None observed.

*Sepals.*—Quantity per flower: Typically eight. Length: About 5 mm. Width: About 1 mm. Shape: Narrowly ovate. Apex: Narrowly acute. Margin: Entire. Texture, upper and lower surfaces: Smooth, glabrous. Color: When opening, upper and lower surfaces: Close to N30A to N30B; towards the base, close to 29D. Fully opened, upper and lower surfaces: Close to N30B; towards the base, close to 29D; color does not fade with development.

*Peduncles.*—Length: About 5.7 mm. Diameter: About 3 mm. Angle: Upright to about 45° from vertical. Strength: Moderately strong. Texture: Smooth, glabrous. Color: Close to 162B.

*Reproductive organs.*—Stamens: None observed on plants of the new *Celosia*. Pistils: Quantity per flower: One. Length: About 4 mm. Stigma shape: Club-shaped. Stigma color: Close to 22D. Style length: About 3.5 mm. Style color: Close to 22D. Ovary color: Close to 22D.

*Seeds and fruits.*—Seed and fruit development have not been observed on plants of the new *Celosia*.

Disease & pest resistance: Plants of the new *Celosia* have not been observed to be resistant to pathogens and pests common to *Celosia* plants.

Garden performance: Plants of the new *Celosia* have been observed to have good garden performance and tolerate rain, wind and high temperatures of about 35° C. and to be hardy to USDA Hardiness Zone 9.

It is claimed:

1. A new and distinct *Celosia* plant named 'BKCELOR' as illustrated and described.

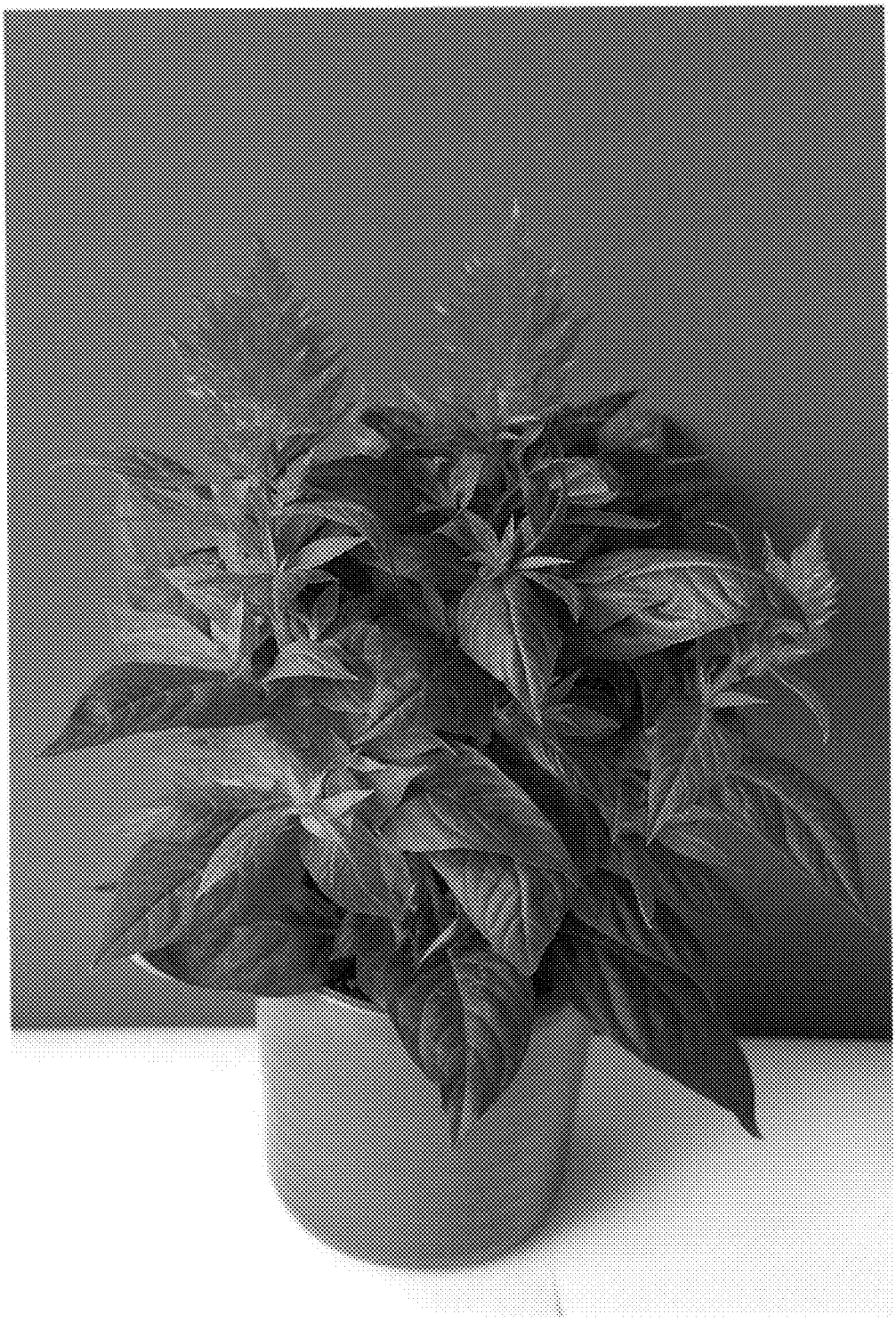

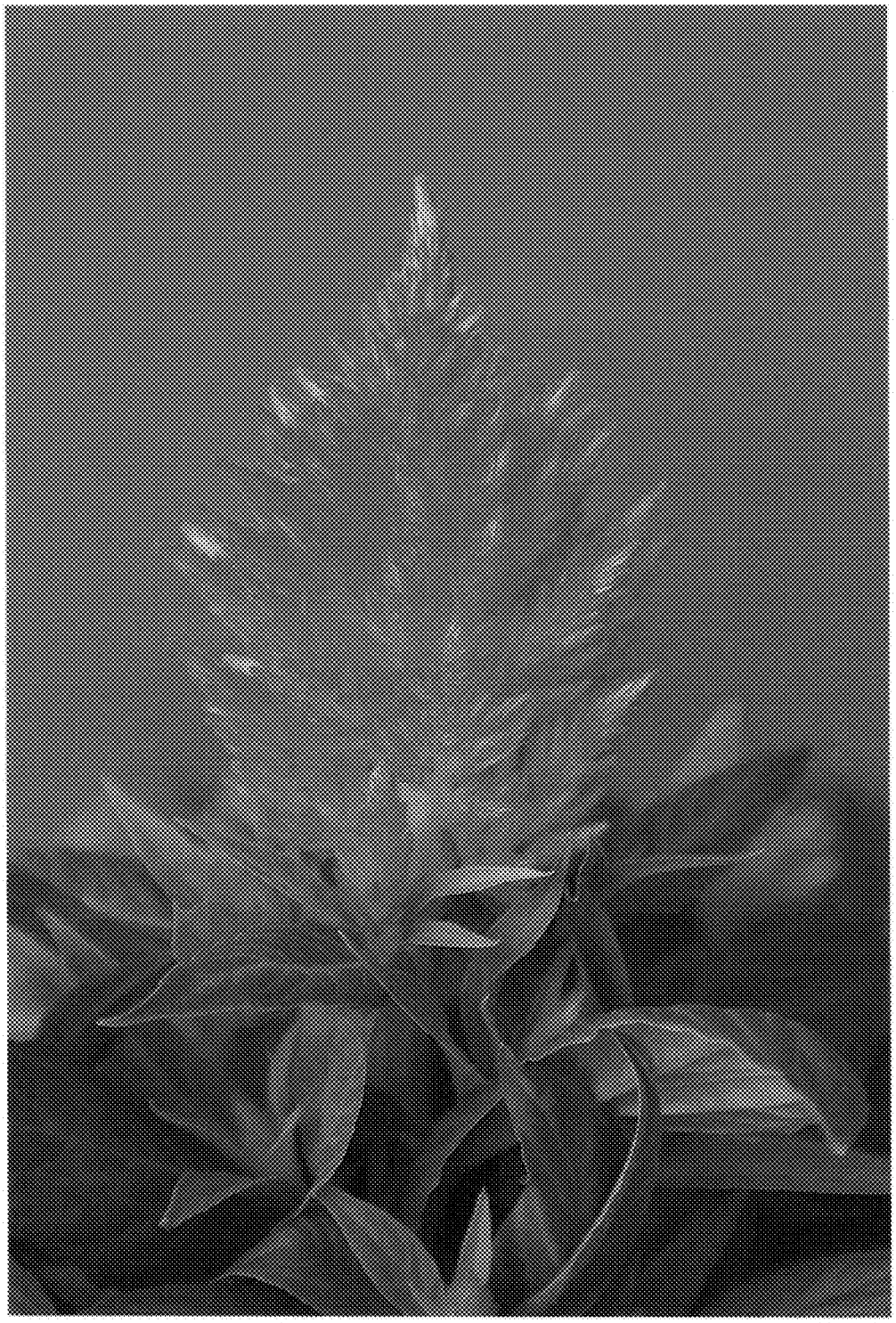

* * * * *